United States Patent
Gümbel et al.

(10) Patent No.: US 7,074,922 B2
(45) Date of Patent: Jul. 11, 2006

(54) METHOD FOR PRODUCING THE TAUTOMERIC FORM OF (1) OF 2,4,6-TRIANILINO-P-(CARBO-1'-ETHYLHEXYL-1'OXYL)-1, 3, 5-TRIAZINE

(75) Inventors: Helmut Gümbel, Dannenfels (DE); Heinz-Josef Kneuper, Niederkirchen (DE); Rainer Becker, Bad Dürkheim (DE); Gerhard Bertlein, Neckargemünd (DE); Michael Drögemüller, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/503,305

(22) PCT Filed: Feb. 26, 2003

(86) PCT No.: PCT/EP03/01931

§ 371 (c)(1),
(2), (4) Date: Aug. 3, 2004

(87) PCT Pub. No.: WO03/074499

PCT Pub. Date: Sep. 12, 2003

(65) Prior Publication Data

US 2005/0143577 A1    Jun. 30, 2005

(30) Foreign Application Priority Data

Mar. 1, 2002  (DE) ................. 102 08 840

(51) Int. Cl.
C07D 251/70   (2006.01)
A61K 7/42     (2006.01)

(52) U.S. Cl. ...................... 544/197; 424/401

(58) Field of Classification Search ............... 544/197; 424/59, 401
See application file for complete search history.

(56) References Cited

U.S. PATENT DOCUMENTS 4,617,390 A   10/1986  Hoppe et al.
4,656,272 A    4/1987  Martin et al.

FOREIGN PATENT DOCUMENTS

DE   35 18670   11/1986
EP    087 098    8/1983
EP    202 611   11/1986

OTHER PUBLICATIONS

Advances in Heterocyclic Chemistry, Supplement 1, The Tautomerism of Heterocycles, Academic Press New York, 1976, Kp 2, S. 168.

*Primary Examiner*—Venkataraman Balasubramanian
(74) *Attorney, Agent, or Firm*—Novak Druce & Quigg, LLP; Jason D. Voight

(57) ABSTRACT

The invention relates to a method for producing the tautomeric form (I) of 2,4,6-trianilino-p-(carbo-2'-ethylhexyl-1'-oxy)-1,3,5-triazine by the crystallization of a tautoner mixture in the presence of one or more solvents selected from the group consisting of aliphatic alcohol having 2 8 C-atoms made of aliphatic alcohol, aliphatic carboxylic acid alkyl esters having a total of between 3–10 C-atoms, aromatic carboxylic acid alkyl esters having a total of between 8–12 C-atoms, aliphatic carboxylic acid esters having a total of between 3 9 C-atoms, carboxylic acid nitriles having a total of between 2–8 C-atoms, dialkylketones having a total of between 3–6 C-atoms and aliphatic sulphones having a total of between 3–6 C-atoms. The solvent or solvent mixture can additionally contain up to 30 wt % of a hydrocarbon (I) acts as a light protecting agent in cosmetic preparations.

3 Claims, 1 Drawing Sheet

METHOD FOR PRODUCING THE TAUTOMERIC FORM OF (1) OF 2,4,6-TRIANILINO-P-(CARBO-1'-ETHYLHEXYL-1'OXYL)-1, 3, 5-TRIAZINE

The present invention relates to a novel process for the preparation of the tautomeric form I of 2,4,6-trianilino-p-(carbo-2'-ethylhexyl-1'-oxy)-1,3,5-triazine

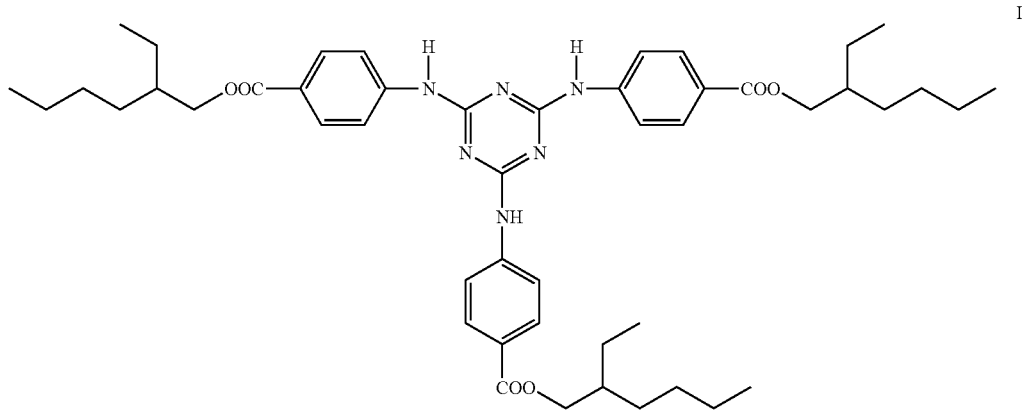

by crystallization from a tautomer mixture.

The invention also relates to the use of the form I isolated in this way as light protection agent in cosmetic preparations.

EP-B 087 098 (1) describes the preparation of 2,4,6-trianilino-p-(carbo-2'-ethylhexyl-1'-oxy)-1,3,5-triazine from cyanuric chloride and 2-ethylhexyl p-aminobenzoate, and the purification of the crude product by recrystallization from petroleum spirit.

DE-A 35 18 670 (2) relates to the use of esters of a branched alkanoic acid having 6 to 10 carbon atoms and a saturated aliphatic alcohol having 10 to 20 carbon atoms as solvent in the preparation of s-triazine derivatives such as 2,4,6-trianilino-p-(carbo-2'-ethylhexyl-1'oxy)-1,3,5-triazine.

The products which form in said processes are generally tautomer mixtures, as can be readily deduced from the relevant IR spectra. It is known, for example from J. Elguero, C. Marzin, A. R. Katritzky and P. Linda, Advances in Heterocyclic Chemistry, Supplement 1, The Tautomerism of Heterocycles, Academic Press New York, 1976, Ch. 2, p. 168, that in the case of amino-s-triazine derivatives, tautomers with regard to the NH protons can generally arise.

The use of the 2,4,6-trianilino-p-(carbo-2'-ethylhexyl-1'-oxy)-1,3,5-triazine tautomer mixtures obtained in this way in cosmetic preparations often leads to the problem of the substance which has passed into solution in the cosmetic oils used gradually settling out again upon storage.

In addition, it is important for the user that the substance is chemically uniform during the test for its suitability for the application and during the application itself. Particularly for toxicological investigations and compatibility tests, the results of which are naturally of particular relevance for ingredients of cosmetic preparations, mixtures of substances of varying physical properties, i.e. including tautomer mixtures, cannot be used because in feeding experiments with them on living organisms in these test organisms no constant composition can be presupposed, meaning that the result of these tests could consequently be falsified. In addition, such mixtures are often subject to great variation in the composition due to even minute changes to the preparation conditions, meaning that a certain composition can only be reproduced with difficulty.

It is an object of the present invention to overcome the disadvantages described when using 2,4,6-trianilino-p-(carbo-2'ethylhexyl-1'-oxy)-1,3,5-triazine.

We have found that this object is achieved by a process for the preparation of the tautomeric form I of 2,4,6-trianilino-p-(carbo-2'-ethylhexyl-1'-oxy)-1,3,5-triazine by crystallization from a tautomer mixture in the presence of one or more solvents chosen from the group consisting of aliphatic alcohols having 2 to 8 carbon atoms, aliphatic carboxylic alkyl esters having a total of 3 to 10 carbon atoms, aromatic carboxylic alkyl esters having a total of 8 to 12 carbon atoms, aliphatic carbonic esters having a total of 3 to 9 carbon atoms, carbonitriles having a total of 2 to 8 carbon atoms, dialkyl ketones having a total of 3 to 6 carbon atoms and aliphatic sulfones having a total of 3 to 6 carbon atoms, where the solvent or the solvent mixture may additionally comprise up to 30% by weight of a hydrocarbon.

Suitable aliphatic alcohols having 2 to 8 carbon atoms are straight-chain, branched alcohols and also cyclic alcohols. Examples which may be mentioned are ethanol, n-propanol, isopropanol, n-butanol, tert-butanol, n-pentanol, n-hexanol, n-octanol, 2-ethylhexanol and cyclohexanol. An alcohol which is preferably used as solvent is ethanol.

Suitable aliphatic carboxylic alkyl esters having a total of 3 to 10 carbon atoms are, for example, straight-chain carboxylic esters, such as ethyl formate, n-propyl formate, methyl acetate, ethyl acetate, n-propyl acetate, n-butyl acetate, methyl butyrate, ethyl butyrate, n-propyl butyrate and n-butyl butyrate. Preference is given to aliphatic carboxylic alkyl esters having a total of 3 to 6 carbon atoms, particularly to ethyl acetate.

Aromatic carboxylic alkyl esters having a total of 8 to 12 carbon atoms are to be understood as meaning, for example, methyl benzoate, ethyl benzoate, n-propyl benzoate, isopropyl benzoate, n-butyl benzoate, tert-butyl benzoate, preferably methyl benzoate.

Aliphatic carbonic esters having a total of 3 to 9 carbon atoms which may be mentioned are dimethyl carbonate, diethyl carbonate, di-n-propyl carbonate, diisopropyl carbonate, di-n-butyl carbonate and propylene carbonate, preferably dimethyl carbonate.

Suitable carbonitriles having a total of 2 to 8 carbon atoms are, for example, acetonitrile, propionitrile, n-butyronitrile, benzonitrile, preferably acetonitrile.

Suitable dialkyl ketones having a total of 3 to 6 carbon atoms are, inter alia, straight-chain, branched and cyclic dialkyl ketones, for example acetone, butanone, 2-pentanone, 3-pentanone, 2-hexanone, 3-hexanone and cyclohexanone, preferably acetone.

A representative of aliphatic sulfones having a total of 3 to 6 carbon atoms which may be mentioned is, for example, tetramethylene sulfone.

The hydrocarbons optionally coused as cosolvent can either be aliphatic hydrocarbons, such as pentane, hexane, petroleum ether, ligroin or cyclohexane and/or aromatic hydrocarbons, such as toluene or xylene. These hydrocarbons can be present in an amount up to 30% by weight, preferably in an amount of not more than 10% by weight.

A preferred embodiment of the process according to the invention involves the crystallization being carried out in one of the aliphatic alcohols having 2 to 4 carbon atoms mentioned at the start, in one of the aliphatic carboxylic alkyl esters having a total of 3 to 6 carbon atoms mentioned at the start, or a mixture thereof.

The crystallization is particularly preferably carried out in ethanol, ethyl acetate or a mixture thereof as solvent.

The solvents used for the purposes of the present invention can either be anhydrous or else have a water content of at most 10% by weight, preferably of at most 5% by weight, particularly preferably of at most 2% by weight. This is true in particular for the abovementioned aliphatic alcohols and for the aliphatic carboxylic alkyl esters.

The recrystallization is generally carried out by dissolving the tautomer mixture in the solvent or the solvent mixture at temperatures of from 40 to 120° C., preferably 60 to 100° C. The amount of solvent is expediently 100 to 2000% by weight, preferably 150 to 600% by weight, based on the tautomer mixture. After insoluble components have been filtered off at elevated temperature, the couse of filtration auxiliaries being advisable, the tautomeric form I is separated off by crystallization at temperatures of from approximately 15 to 40° C. Since I tends to form supersaturated solutions, the addition of seed crystals is expedient at this temperature. Filtration, drying and optionally formulation are carried out in accordance with customary methods.

The tautomer mixture used is expediently admixed directly as a melt with said solvent or solvent mixture. However, the tautomer mixture can also be introduced into the hot solvent in crystallized form or can be heated together with this solvent.

The tautomeric form I is stable as such and, in solid and in dissolved form, does not convert back to the tautomer mixture.

The present invention further provides for the use of the tautomeric form I isolated in this way as light protection agent in cosmetic preparations. Examples of the compositions of such cosmetic preparations, such as light protection emulsions, oil-in-water light protection creams, water-in-oil light protection creams or light protection foams are given in the patent specification (1).

Customary cosmetic oils which are used as solvent for I are, in addition to the $C_6$–$C_{10}$-alkanoic acid $C_{10}$–$C_{20}$-alkyl esters, which form the basis of the patent publication (2), such as cetylstearyl 2-ethylhexanoate, for example groundnut oil, olive oil, isopropyl stearate, isopropyl myristate, coconut fatty acid triglycerides, caprylic-capric triglyceride, triethyl citrate, polyethylene glycol glyceryl cocoate, diisopropyl adipate, propoxylated myristyl alcohol or mixtures thereof. The solubilities of the tautomeric form I in said cosmetic oils is sufficiently high. The storage stability of these solutions with regard to clouding and precipitation is significantly better because the solutions remain clear over a prolonged period.

A further advantage of the process according to the invention is the good crystallizability and, associated therewith, the good filterability and good drying behavior of the tautomerically pure product.

EXAMPLE 1

Preparation of the Tautomeric Form I by Recrystallization from Ethanol 250 kg of s-trichlorotriazine (corresponding to 1.36 kmol) were reacted with 1025 kg of 2-ethylhexyl p-aminobenzoate (corresponding to 4.11 kmol) in xylene as solvent to give the 2,4,6-trianilino-p-(carbo-2'-ethylhexyl-1'-oxy)-1,3,5-triazine tautomer mixture.

After the solvent had been distilled off, 4500 kg of ethanol (corresponding to 400% by weight, based on the tautomer mixture used) were added to the 115° C.-hot melt over the course of 5 to 6 hours, the temperature being maintained between 65 and 80° C. Following the addition of 25 kg of a customary filtration auxiliary (Celite®), insoluble components were filtered off at 65 to 70° C. and the solution was cooled to 20° C. Then, by seeding with 150 kg of the tautomeric form I (coarsely crystalline, undried product from an earlier batch corresponding to 110 kg of dry product), crystallization was initiated. After stirring for 18 hours at 20° C., the product was discharged via a centrifuge, washed with ethanol and dried at 60° C./20 mbar. This gave 915 kg of tautomerically pure I (72% yield, based on s-trichlorotriazine used and after deducting the amount of seed crystal).

Figure 1:
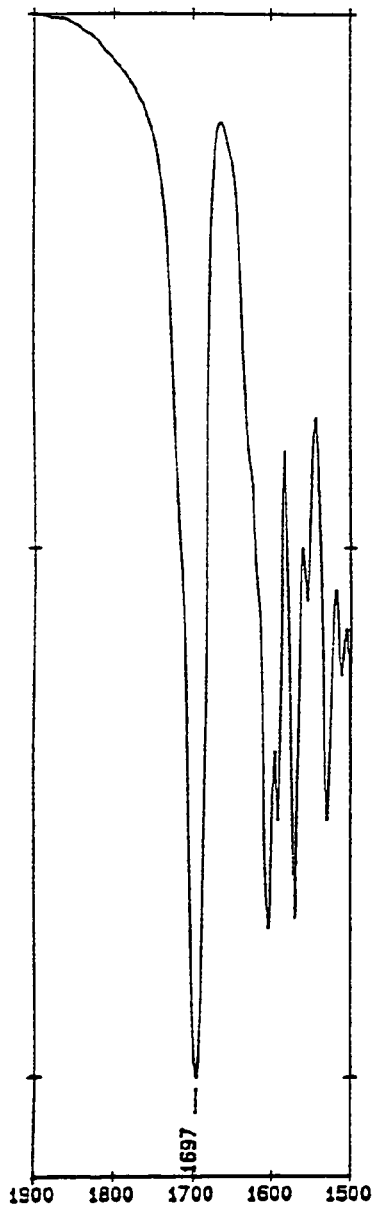
FIGS. 1 and 2 show a characteristic range of the IR spectrum of the tautomeric form I.

The IR spectrum of the product (KBr pellet) showed, in the range of the carbonyl stretching vibrations, only one band for the carboxyl groups at 1697 $cm^{-1}$ (see FIG. 1) in contrast to the corresponding double band for the product from Comparative Example A.

EXAMPLE 2

Preparation of the Tautomeric Form I by Recrystallization from Ethyl Acetate

Analogously to Example 1, the recrystallization was carried out with 400% by weight of ethyl acetate, based on the tautomer mixture used. The tautomerically pure product was obtained in a yield of 58%.

Figure 2:
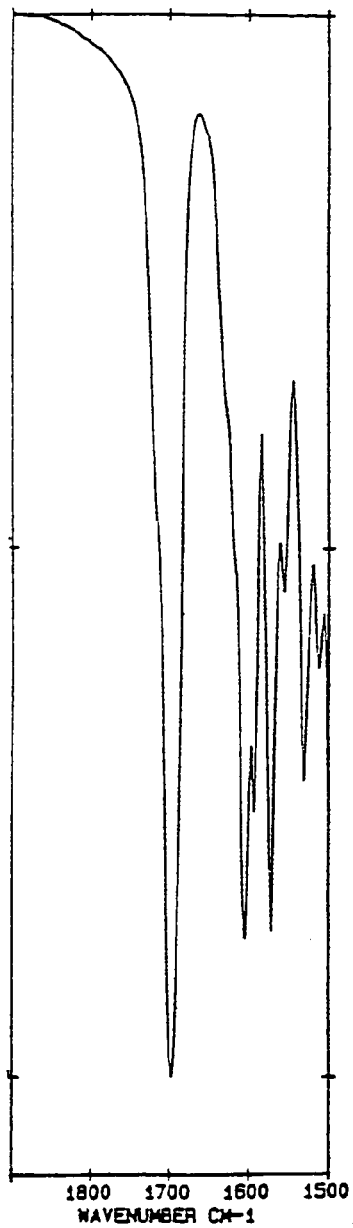

The IR spectrum of the product (KBr pellet) showed, in the range of the carbonyl stretching vibrations, only one band for the carboxyl groups at 1697 $cm^{-1}$ (see FIG. 2) in contrast to the corresponding double band for the product from Comparative Example A.

EXAMPLES 3 TO 12

Analogously to Example 1, the recrystallization was carried out in each case with ethylhexanol (Ex. 3), cyclohexanol (Ex. 4), methyl benzoate (Ex. 5), tetramethylenesulfone (Ex. 6), dimethyl carbonate (Ex. 7), methyl ethyl ketone (Ex. 8), acetonitrile (Ex. 9) and acetone (Ex. 10), and with solvent mixtures of 90% by weight of ethanol/10% by weight of xylene (Example 11) and 90% by weight of ethyl acetate/10% by weight of xylene (Example 12).

The IR spectra of the products isolated in each case (KBr pellet) likewise showed, in the range of the carbonyl stretching vibrations, only one band for the carboxyl groups at 1697 cm$^{-1}$.

COMPARATIVE EXAMPLE A

Recrystallization from Petroleum Spirit

According to the patent specification (1), the tautomer mixture produced in the preparation was recrystallized from petroleum spirit with boiling limits from 120 to 130° C.

Figure 3:
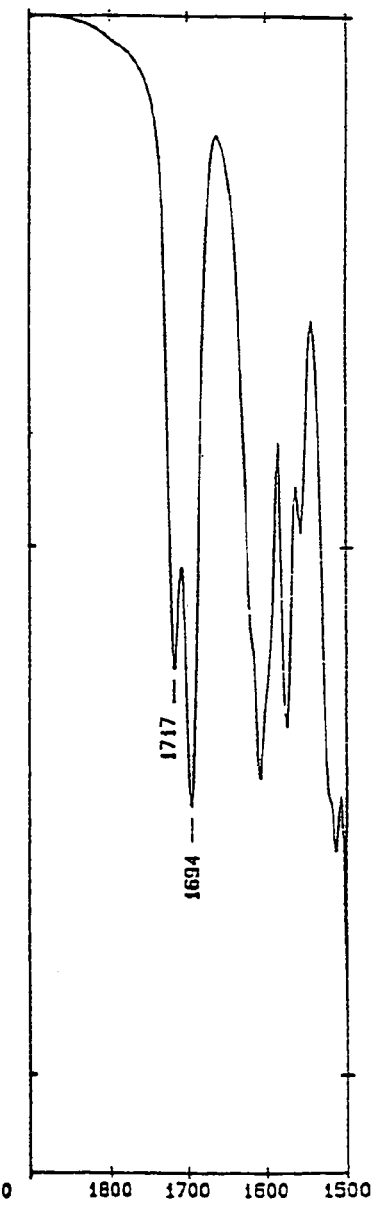
FIG. 3 shows the IR spectrum of the tautomoric miflure in the same range.

The IR spectrum of the product (KBr pellet) shows, in the range of the carbonyl stretching vibrations, a double band for the carbonyl groups at 1717/1694 cm$^{-1}$ (see FIG. 3), which is to be regarded as proof of the presence of two tautomeric forms. The IR spectrum for the tautomer mixture prior to recrystallization was essentially identical to this spectrum.

EXAMPLE 13

Storage Stability of Solutions of the Tautomeric Form I in Cosmetic Oils

The tautomerically pure compound I was dissolved in each case in $C_8$–$C_{10}$-coconut fatty acid triglyceride (solubility 5.8 g per 100 g of oil) and cetylstearyl 2-ethylhexanoate (solubility 1.0 g per 100 g of oil). Both solutions were still clear after 2 days.

By contrast, corresponding initially clear solutions of the tautomer mixture with a widely varying content of I became cloudy after just 1 day, and precipitations were evident after just 2 days.

We claim:

1. A process for the preparation of the tautomeric form I of 2,4,6-trianilino-p-(carbo-2'-ethylhexyl-1'-oxy)-1,3,5-triazine

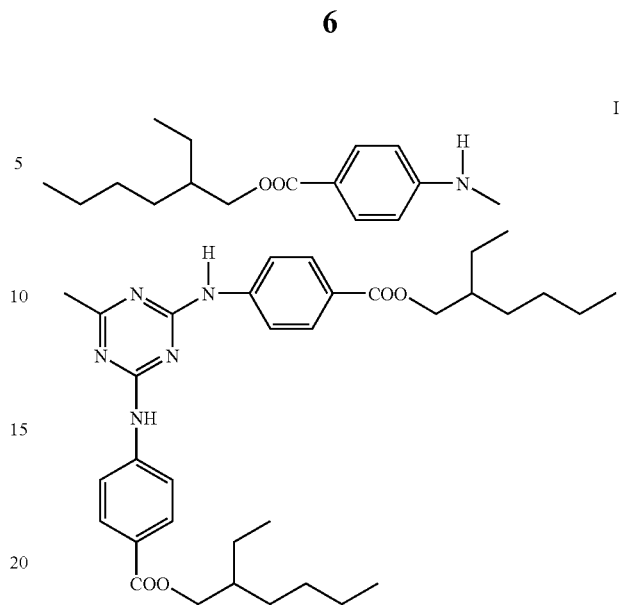

by crystallization from a tautomer mixture in the presence of one or more solvents chosen from the group consisting of aliphatic alcohols having 2 to 8 carbon atoms, aliphatic carboxylic alkyl esters having a total of 3 to 10 carbon atoms, aromatic carboxylic alkyl esters having a total of 8 to 12 carbon atoms, aliphatic carbonic esters having a total of 3 to 9 carbon atoms, carbonitriles having a total of 2 to 8 carbon atoms, dialkyl ketones having a total of 3 to 6 carbon atoms and aliphatic sulfones having a total of 3 to 6 carbon atoms, where the solvent or the solvent mixture may additionally comprise up to 30% by weight of a hydrocarbon.

2. A process as claimed in claim 1, wherein the crystallization is carried out in an aliphatic alcohol having 2 to 4 carbon atoms, in an aliphatic carboxylic alkyl ester having a total of 3 to 6 carbon atoms or a mixture thereof.

3. A process as claimed in claim 1, wherein the crystallization is carried out in ethanol, ethyl acetate or a mixture thereof.

* * * * *